United States Patent [19]

Hawiger et al.

[11] Patent Number: 4,703,039

[45] Date of Patent: Oct. 27, 1987

[54] METHOD OF PRODUCING BIOLOGICALLY ACTIVE MOLECULES HAVING EXTENDED LIFE TIME

[75] Inventors: Jack J. Hawiger, Chestnut Hill; Sheila Timmons, Boston; Marek Kloczewiak, Jamaica Plain, all of Mass.

[73] Assignee: New England Deaconess Hospital Corporation, Boston, Mass.

[21] Appl. No.: 786,241

[22] Filed: Oct. 9, 1985

Related U.S. Application Data

[63] Continuation-in-part of Ser. No. 598,711, Apr. 10, 1984, Pat. No. 4,666,884.

[51] Int. Cl.[4] .................. A61K 37/02; C07K 1/00
[52] U.S. Cl. ................................. 514/21; 530/333
[58] Field of Search ............... 260/112.5 R; 514/21; 530/333

[56] References Cited

U.S. PATENT DOCUMENTS

| | | | |
|---|---|---|---|
| 4,220,722 | 9/1980 | Rowley et al. | 260/112.5 R |
| 4,221,777 | 9/1980 | Nishino | 260/112.5 R |
| 4,275,000 | 6/1981 | Ross | 260/112.5 R |
| 4,303,592 | 12/1981 | Laura et al. | |
| 4,351,337 | 9/1982 | Sidman | |
| 4,384,995 | 5/1983 | Stevens | 260/112.5 R |
| 4,423,034 | 12/1983 | Nakagawa et al. | 260/112.5 R |
| 4,454,065 | 6/1984 | Gilvarg et al. | 260/112.5 R |
| 4,455,290 | 6/1984 | Olexa et al. | |
| 4,476,116 | 10/1984 | Anik | |
| 4,479,898 | 10/1984 | Gilvarg et al. | 260/112.5 R |
| 4,479,940 | 10/1984 | Bizzini | 260/112.5 R |
| 4,525,300 | 6/1985 | Yoshida et al. | 260/112.5 R |
| 4,545,931 | 10/1985 | Houghton | 260/112.5 R |

OTHER PUBLICATIONS

Chem. Abstr. vol. 103, (1985) 48770y.
Chem. Abstr. vol. 83, (1975) 127189n.
Chem. Abstr. vol. 96, (1981) 168576y.
Chem. Abstr. vol. 97, (1982) 179864n.
Chem. Abstr. vol. 102, (1985) 181700w.
Chem. Abstr. vol. 103, (1985) 134219g.
Peptides and Proteins as Drugs., Ferraiolo, Bobbe L. and Benet, Leslie Z., Dept. Pharm., Univ. of California, San Francisco, Calif. 94143 USA, Pharmaceutical Research, 1985, (4), 151–156 (Eng.).
Biochemistry, 1982 vol. 21, No. 6, pp. 1414–1420—Isolation, Characterization and Synthesis of Peptides from Human Fibrinogen that Block the Straphylococcal Clumping Reaction and Construction of a Synthetic Particle.
Biochemical and Biophysical Research Communications, vol. 107, No. 1, Jul. 16, 1982 pp. 181–187—Localization of a Site Interacting with Human Platelet Receptor on Carboxy-Terminal Segment of Human Fibrinogen Chain.
Thrombosis Research 29; 249–255, 1983—Fibrinogen Site for Platelets.

*Primary Examiner*—Delbert R. Phillips
*Attorney, Agent, or Firm*—Lahive & Cockfield

[57] ABSTRACT

The disclosure concerns a synthetic conjugate, methods of constructing this conjugate, and methods of using a conjugate of this type to replace naturally occurring proteins or inhibiting the reaction between a naturally occurring protein and a defined site of biological activity in a vertebrate.

19 Claims, 12 Drawing Figures

FIG. 4
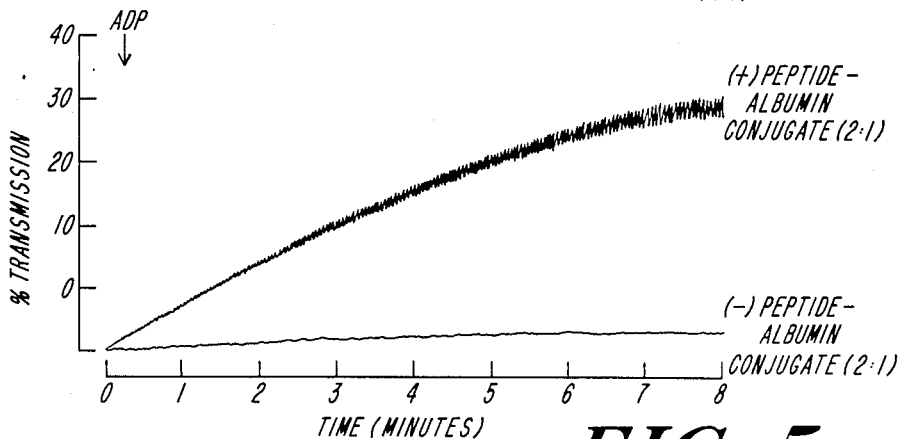
FIG. 5
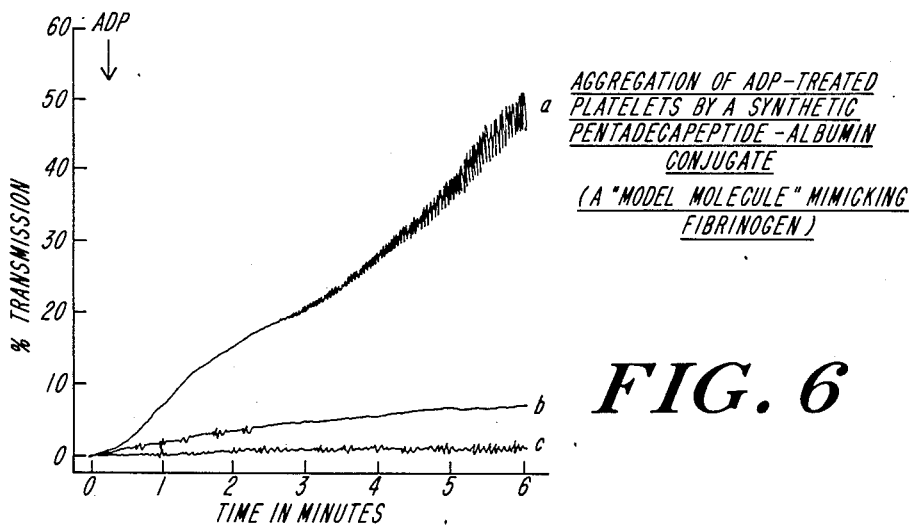
FIG. 6

METHOD OF PRODUCING BIOLOGICALLY ACTIVE MOLECULES HAVING EXTENDED LIFE TIME

The invention described herein was made, in part, in the course of work under research grants HL-30649 and HL-30648, from the National Institutes of Health, U.S. Public Health Service.

REFERENCE TO RELATED APPLICATIONS

The present application is a continuation-in-part of copending patent application Ser. No. 598,711, filed Apr. 10, 1984 now U.S. Pat. No. 4,666,884. It is also related to copending patent application Ser. No. 599,477, also filed Apr. 10, 1984 now U.S. Pat. No. 4,661,471.

BACKGROUND OF THE INVENTION

The present invention relates to the formation and methods for use of peptide conjugates which interact with specific, defined sites of biological activity in vivo or in vitro. More particularly, the invention relates to a method of forming biologically active molecules which react with a defined site in a vertebrate system and have an extended lifetime in the circulatory system.

The biochemical systems of a vertebrate body act by interaction of various biological molecules. Generally, the sites of interaction are relatively small even though the size of the total molecule involved in the interaction may be very large. For example, although many proteins such as enzymes have a molecular weight in the ten to one hundred thousand dalton range formed of hundreds to thousands of amino acid residues, the actual active site is normally comprised of one or a few specifically positioned amino acid residues. Because of the small size of these sites of biologic activity, small peptides which mimic the active site can be used to inhibit or act in place of the active sites of these larger molecules. These small peptides can react with a variety of protein or lipid molecules including binding proteins, inhibitory proteins, hormones, cofactors, activators and cell membrane sites (receptors). Because of this capacity to interact with functionally important sites, these peptides can be used as pharmaceutical agents.

The vertebrate body has a series of natural defenses, including the immune system, which clears the blood stream of a variety of molecules. A small peptide, for example twenty amino acid residues or less, is normally cleared within minutes. However, naturally occuring larger molecules, e.g., large proteins such as human serum albumin, immunoglobulins and other molecules which cause little or no immunogenic response in a vertebrate have an extended lifetime in the circulatory system; the lifetime may be from three to as much as forty-five days.

One of the problems with molecules which are cleared quickly from the bloodstream is that to obtain a pharmaceutical or other beneficial effect, a specific range of concentration is needed. To achieve this concentration range with molecules that are cleared quickly, two general methods of maintaining the level have been used; a mechanical device or a controlled release system. Mechanical devices such as infusion pumps or intravenous units are used to add material to the bloodstream at a rate which parallels the clearance rate of the material. The device obtains the material from a large reservoir and supplies it to the body at a constant rate.

The alternative is some form of controlled release implant or device. These controlled release devices are based on either of two distinct schemes: the material is trapped or bound in a device which has pores and allows the release of the material by an osmotic pressure method; or the material is trapped or bound in a material or membrane which is hydrolyzed or broken down slowly by chemical reactions in the bloodstream. Examples of the first of these methods are microcapsules or other forms of encapsulated hormone or drugs. Examples of the second type are such shown in Sidman patent, U.S. Pat. No. 4,351,337 which discloses a biodegradable implantable drug delivery system where enzymes destroy the walls of the carrier at a substantially controlled rate, allowing controlled rate release of the material into the bloodstream.

Both of these methods of attempting to achieve the substantially constant level of material in the bloodstream have attendant problems. The mechanical methods of achieving this end require a reservoir as well as possibly limiting the mobility of the infused animal or person. Mechanical methods also rely on devices which may break down in time. Methods for controlled rate release using implantable or oral receptacles which release the material based on osmotic pressure or by controlled hydrolysis or breakdown of a membrane also have substantial problems. These products usually do not have true zero order kinetic release and, therefore, there is some variation in the amount of material in the bloodstream of the animal. In osmotic devices, there is normally a higher outflow rate at the time of the implant while in the hydrolysis or breakdown methods, the initial rate will normally be lower while the final rate will be higher as hydrolysis or breakdown of the membrane releases more and more pockets of the material. Since most pharmaceutical preparations need an extended lifetime for activity, there would be an advantage in producing molecules which interact with the sites of biological activity, such as the small peptides, but have the extended lifetime of the larger, macromolecular molecules.

Accordingly, it is an object of the invention to provide a method of producing a biologically active material which has extended lifetime in the circulatory system without the need of mechanical infusion systems or degrading membranes. Another object of the invention is to provide a molecule which has specific activity with functionally important sites of proteins and lipids, particularly in cell membranes, while having an extended lifetime in the circulatory system. A further object of the invention is to provide a method of forming a synthetic molecule which will interact with defined sites of biological activity in a vertebrate and have an extended lifetime in the circulatory system. These and other objects and features of the inventions will be apparent from the summary of the invention, the drawing and the description.

SUMMARY OF THE INVENTION

The present invention features a synthetic conjugate, methods of constructing this conjugate, and methods of using a conjugate of this type to replace naturally occuring proteins or inhibiting the reaction between a naturally occuring protein and a defined site of biological activity in a vertebrate. The conjugate is formed of one or more peptides and a carrier molecule selected from a group consisting of proteins, polysaccharides, lipids, glycolipids, phospholipids, and neutral lipids.

Generally, the carrier molecule is non-immunogenic in the vertebrate, although in some cases it may be immunogenic. Each of the peptides is complementary with at least one defined site of biological activity in a vertebrae. As used herein, the term "defined site of biological activity", means a site of interaction between a peptide and a protein or lipid including, but not limited to, activator sites, active sites of enzymes, hormonal active sites, binding sites of proteins, cofactor activation sites and cellular receptors. The terms "proteins" or "lipids" as used herein include all derivatives such as glycoproteins, glycolipids, phospholipids, and neutral lipids. Each of the peptides which form part of the conjugate have a characteristic half life in the circulatory system of the vertebrate. The conjugate, which is a composite of one or more peptides and the carrier molecule, is reactive with at least one of the defined sites of biological activity in the vertebrate. The conjugate is characterized by half life in the circulatory system of the vertebrate which is substantially longer than the half life of the peptide attached thereto. The preferred conjugation method is by a sulfhydryl group as a link but other methods of chemical bonding can be used for conjugation, including but not limited to an amino group as a link. The carrier molecule is preferably selected from a group consisting of albumin, immunoglobulin and other proteins. The carrier molecule may have only one of the peptides conjugated thereto (a monovalent conjugate) or may have two or more side chains (di- or polyvalent). If two or more distinct peptides are conjugated to the same carrier molecule, they may be complementary with different sites of biological activity.

As noted, the invention also features an in vivo method of using a conjugate to replace a naturally occurring protein which possesses at least one biologically important in vivo function in a vertebrate. The conjugate is formed as previously described and can functionally replace the naturally occuring protein in reactions with at least one of the defined sites of biological activity in the vertebrate. The method includes the step of administering this specific conjugate to the vertebrate, thereby allowing the conjugate to replace the naturally occurring protein in functional reactions. For example, using a carrier molecule with two or more peptides having the same functional activity, e.g., interaction with blood vessel walls, blood clots or thrombi may be formed which may be linked to the vessel walls. As such, these conjugates could act as synthetic von Willebrand factor or other polyvalent molecules. If only a single peptide is attached to the backbone or there are peptides which are complementary to distinct sites, the conjugate can be used as an inhibitory molecule, inhibiting the reaction of molecules which require linking.

BRIEF DESCRIPTION OF THE DRAWING

FIG. 4 is a schematic drawing a divalent peptide-albumin conjugate, a conjugate which has two peptide molecules per albumin carrier molecule;

FIG. 5 is a graph showing the aggregation effect of a divalent conjugate of a synthetic peptide and albumin;

FIG. 6 illustrates the aggregation effect of a polyvalent conjugate using different peptides conjugated to an albumin backbone;

DESCRIPTION

The present invention concerns a biologically active molecule which is reactive in vivo with sites on proteins or lipids. These molecules are conjugates of a peptide which is complementary to the specific site and a macromolecular backbone such as a protein, dextran, or other non-immunogenic large size molecule. The macromolecule, designated a carrier molecule, has the property that it does not cause undue immunogenic response in the same species and has an extended lifetime within the circulatory system of the vertebrate. In contrast, the small, active portion of the conjugated molecule is a peptide which has a very short, e.g., on the order of minutes, half life within the circulatory system. The conjugate of the peptide and carrier molecule has the property of the extended lifetime in the circulatory system of the carrier molecule while providing the specificity of the peptide. Although any conjugate which has the extended lifetime and the activity of the specific peptide or peptides is within the scope of the invention described herein, the carrier molecule may in some cases itself perform various biological functions.

In its broadest aspect, the invention is contemplated to include a large family of conjugated molecules which have the carrier molecule backbone and one or more peptides conjugated to it. This family of conjugates can be used for a variety of purposes including, but not limited to, replacement for naturally occuring molecules, replacement for natural inhibitors, replacement for molecules which function as cellular ligands, or as extended lifetime pharmaceutical preparations. If a single peptide is bound to the carrier molecule, the resultant monovalent conjugate is most useful as a pharmaceutical preparation in a form of an inhibitory agent. In either case, the single peptide attached to the conjugate reacts with the defined site of biological activity as if the conjugate were a naturally occuring molecule.

Figure 1:
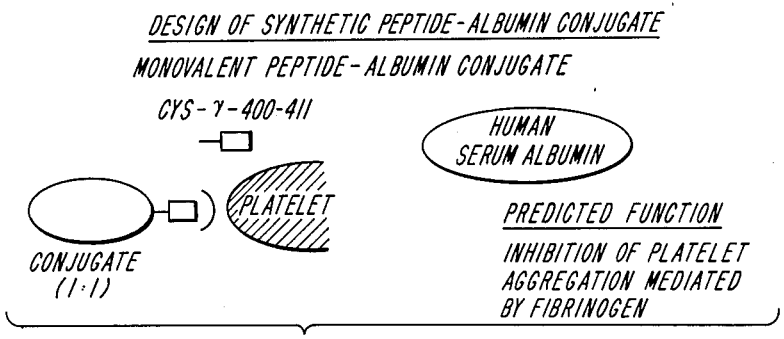
FIG. 1 is a schematic illustration of a monovalent peptide-albumin conjugate.

FIG. 1 illustrates the design of a monovalent conjugate having a single peptide conjugated to a carrier molecule. Because of the one to one peptide/carrier molecule ratio, the monovalent molecule is well adapted for inhibiting reactions. The specific monovalent conjugate illustrated is a sulfhydryl-linked conjugate of a 13-residue peptide ending in cysteine conjugated to human serum albumin. More specifically, the peptide has residues 400–411 from the carboxyl terminal portion of the gamma chain of human fibrinogen with a cysteine residue attached to the amino terminal end. The conjugate, illustrated as the large carrier molecule linked to the peptide, inhibits the platelet aggregation mediated by fibrinogen by reacting with a receptor site on the platelet.

Once formed, the conjugate can be used in a variety of reactions. If more than one peptide having the same specificity is conjugated to a single backbone, polyvalent reactions are possible, whereby the conjugate acts as a multiple site ligand between two identical molecules. If two or more distinct peptides are conjugated to the same backbone, the conjugate may act in a variety of reactions or it may link different molecules or active sites in the same molecule. If different peptides are bound to the carrier molecule at equivalents, the conjugate could act as an additive inhibitor of more than one reaction. This inhibitory property is particularly important in pharmaceutical preparations.

The examples elucidate the concept of the invention. Example 1 illustrates a method of synthesizing peptides which can be linked to the carrier molecule to form a conjugate. Example 2 illustrates a variety of methods of conjugating peptides, such as those synthesized in the method of Example 1, to a macromolecular backbone. These peptides can be linked to the carrier molecule to form either monovalent or polyvalent conjugates. Example 3 illustrates the inhibitory effects of a monovalent conjugate on the fibrinogen-ADP-modified human platelet aggregation reaction. Example 4 illustrates the use of a divalent conjugate as a replacement for a naturally occurring polyvalent molecule, fibrinogen, while Example 5 illustrates the same use for a different polyvalent conjugate.

Example 6 shows that two distinct peptides can have inhibitory effect in the same system if they are complementary to different sites of biological activity. This Example is a preconjugation test which is useful to determine whether the peptides can be conjugated to the same backbone. Example 7 is the counterpoint of Example 6; the same peptide is shown to be complementary with one site of biological activity but not with another. Example 8 illustrates that a chemical modification of a peptide can change its effectiveness. In this Example, the residues necessary for inhibition are unchanged but intermediate residues are changed to modify the hydrophobicity of the peptide. The difference in inhibitory effect is quite evident.

Example 9 is an in vivo test using a conventional test system, the rabbit superior mesenteric artery. It is clear from this test that the peptide which is infused has a dramatic but short term effect on the bleeding time of the rabbit. Example 10 is another model system, an ex vivo perfusion technique. This method uses blood vessel segments to test the effect of the infused material on blood components.

These examples are meant to be purely illustrative and nonlimiting.

EXAMPLE 1

The synthetic peptides described herein were synthesized in a manual shaker apparatus (Chipco Manufacturing) following the solid phase procedure of Barany and Merrifield described in *The Peptides Analysis, Synthesis, and Biology* (Gross and Meinhoper, Eds.), Vol. 2, pp. 1–284 (Academic Press, 1980). An aminomethyl resin (0.45 remol/g) was derivatized with tertbutoxycarbonyl ("Boc")-Val-(4-oxymethyl) phenylacetic acid. The general solid phase synthesis protocol uses the following chemicals: 50% trifluoracetic acid ("TFA") for deprotection, 5% triethylamine for neutralization and a 2–3 fold excess of preformed Boc-amino acid symmetric anhydrides for couplings except for glutamine and histidine residues where direct dicylco-hexylcarbodiimide coupling was used. The level of resin substitution, completeness of coupling, and deprotections were measured by quantitative ninhydrin reactions. The protecting groups and the peptide-resin link were cleaved by reaction in liquid HF/anisole (9:1 v/v) for one hour at 0° C. After evaporation of the HF, the resin was washed twice with ethyl ether, and crude peptides were extracted with 10% acetic acid and freeze-dried. These lyophilized peptides were dissolved in 10% acetic acid, the insoluble material was removed by filtration, and the peptides were purified by high pressure liquid chromatography (HPLC) using a Beckman 430 chromatograph and Whatman preparative column. Absorbed material was washed on the column with 0.1% (w/v) TFA until absorbancy at 214 nm returned to the base line. Then the absorbed peptide was eluted with a linear gradient of acetonitrile, from 0 to 80% concentration with 0.1% TFA, was applied for 100 minutes. The main peptide peak was collected and freeze dried.

EXAMPLE 2(a)

A conjugate of the peptide in Example 1 with human serum albumin was formed after introduction of additional sulfhydryl residues to the amino residues of human serum albumin. In the first procedure, human serum albumin (Miles Laboratories) 10 mg/ml in 0.1 M phosphate buffer, pH 7.8, was modified with a 10-fold molar excess of 17.9 mM N-succinimidyl(4-azidophenyldithio) propionate (Pierce) in dioxane. The reaction was carried out at 4° C. in the dark for one hour before the mixture was dialyzed, in the dark, first against distilled water containing 1 mM mercaptoethanol and then against several changes of distilled water. This procedure is based on the method described by E. F. Vanin and T. H. Jig published in Biochemistry 20:16754, 1981. In the second procedure sulfhydryl residues are introduced into human serum albumin dissolved in 0.1 M phosphate buffer, pH 7.0, using 10-fold molar excess of 2-iminothiolane, dissolved freshly in water, followed by dialysis against distilled water according to the procedure described by R. R. Traut, A. Bollen, T. T. Sun, J. W. B. Hershey, Y. Sondberg and L. R. Pierce, Biochemistry 12:3266, 1973.

These free sulfhydryl residues were used for anchoring the cysteine residue-containing peptide in one of the following ways. (a) Direct oxidation of the mixture of macromolecular carrier and of the 10-fold molar excess of the free cysteine containing-peptide was accomplished by addition of the freshly prepared solution of potassium ferricyanide. The reaction was carried out in 0.05 M Tris-HCl buffer, pH 7.0. After oxidation, the whole mixture was acidified to pH 3.0 with acetic acid and mixed for a few minutes with AG1X8 resin. The resin was centrifuged down or filtered off and the liquid was dialyzed against 0.15 M sodium chloride. (b) Disulfide bond exchange between free sulfhydryl residues of the macromolecular carrier and of the cysteine residues of the peptide modified with 2,2'-dipyridyldisulfide was prepared according to the procedure of D. R. Grassetti & J. F. Murray, Jr., published in Archiv. Biochem. Biophys. 119:41, 1967. Conjugate formation was carried out according to the procedure of J. Carlsson, H. Drevin and R. Axen in Biochem. J. 173:723, 1978, using a two-fold molar excess of peptide toward sulfhydryl residues of the macromolecular carrier.

EXAMPLE 2(b)

In some cases, the peptide to be inserted does not need to have a terminal cysteine. In such cases, the conjugate can be formed by its amino terminal group as a link using classic procedures. Examples of peptides which have been linked to a human serum albumin backbone using these techniques are Ser-Tyr-Asn-Arg-Gly-Asp-Ser-Thr and Arg-Gly-Asp-Ser. These peptides maintain their biologic activity after linking with the serum albumin macromolecular backbone. These peptides can be formed using procedures such as described in Example 1.

EXAMPLE 3

Figure 2:
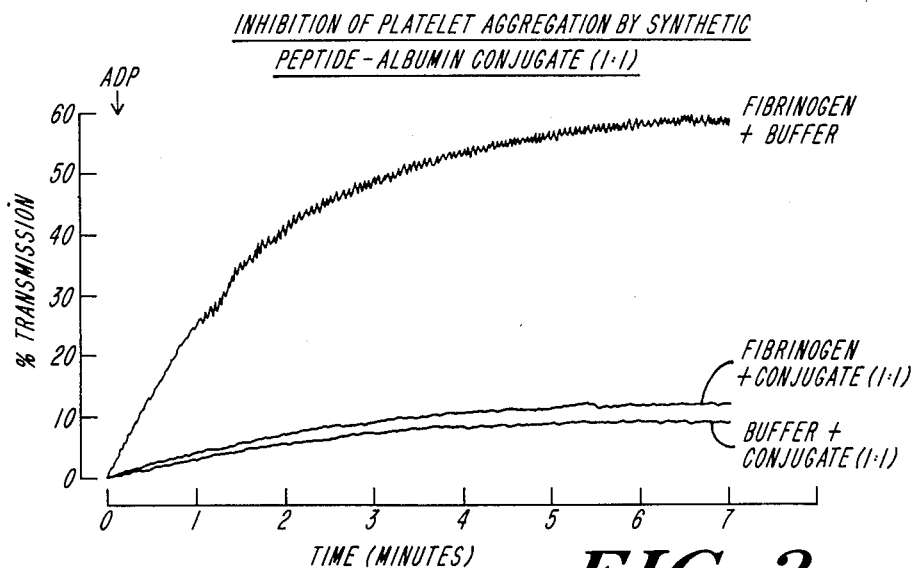
FIG. 2 is a graph illustrating the inhibition of platelet aggregation by a monovalent peptide-albumin conjugate.

This example illustrates that a monovalent conjugate can be useful as an inhibitor of an aggregation reacton. The monovalent conjugate shown in FIG. 1 has a 1:1 ratio of a peptide complementary with the ADP-modified human platelet receptor site for fibrinogen to the human serum albumin backbone. FIG. 2 illustrates the effectiveness of the inhibition caused by this conjugate. The top curve in FIG. 2, labelled fibrinogen+buffer, is a curve showing the change in percent transmission in a in vitro experiment. As human platelets are aggregated by fibrinogen, the transmission increases. The middle curve on FIG. 2 shows the transmission results for a mixture of fibrinogen and the inhibitory conjugate. As is evident from the curve, the percent transmission stays substantially steady state, showing that the aggregation reaction is inhibited. The lowest curve on FIG. 2 shows the change in percent transmission with time for a mixture of the buffer and the conjugate without fibrinogen in the solution. This is to set a baseline level of transmission. As is evident, the conjugate substantially inhibits the fibrinogen reaction, showing that the activity of the conjugate is substantially the same as the activity of the peptide itself.

Figure 3:
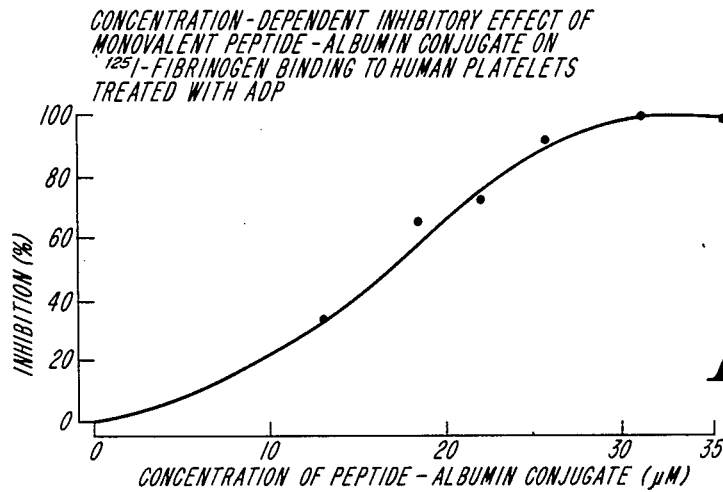
FIG. 3 is a graph illustrating the concentration-dependent inhibitory effect of the same monovalent peptide-albumin conjugate shown in FIG. 2.

FIG. 3 is a graph showing that the inhibitory effect of the same conjugate is concentration dependent. In this experiment, human platelets were treated with ADP and a variety of concentrations of the conjugate were added to affect inhibition of $^{125}$I-fibrinogen binding to the platelets. As the concentration of the conjugate increases, inhibition of binding goes from 0 to almost 100%, showing the effectiveness of the conjugate.

EXAMPLE 4

This Example illustrates that a di- or polyvalent conjugate can be used in place of a naturally occurring molecule which links active sites together. FIG. 4 is a graphic illustration of the design of a divalent molecule having a human serum albumin backbone and the same cysteine peptides as in Example 3. The procedures set forth in Example 2 can be used for attachment of the peptides to the human serum albumin-carrier molecule backbone in either Example 3 or 4. As is evident from the FIGURE, the divalent carrier molecule can react with two sites on different platelets to promote aggregation. This is what done by natural fibrinogen, linking platelets together to form an aggregate.

FIG. 5 illustrates the effectiveness of the divalent conjugate on promoting this inhibition reaction. Human platelets were washed free of fibrinogen and other binding proteins and then treated with ADP. The top curve on FIG. 5 shows the effect of adding the divalent conjugate to the ADP-treated human platelet. As the percent transmission increases with time, aggregates form, acting as if there were fibrinogen in the mixture. The lower curve on FIG. 5 is a control of the identical conjugate with a peptide bound to the human serum albumin that is complementary to the receptor site. As is evident, transmission is substantially unchanged over time, showing that no aggregates are formed by monovalent conjugate without added Fibrinogen.

The peptide used in this example is identical to that used in Example 3, a cysteine residue linked to residues 400–411 of the gamma chain of human fibrinogen.

EXAMPLE 5

This Example illustrates that a polyvalent conjugate can also be manufactured and used in an aggregation reaction. FIG. 6 shows a aggregation of human platelets by a polyvalent conjugate similar, but not identical to that described in connection with Example 4. Multiple copies of a different peptide, residues 397–411 of the gamma chain of fibrinogen bound to a cysteine residue were conjugated to a human serum albumin backbone. Curve a on FIG. 6 illustrates the aggregation of ADP-treated human platelets by this polyvalent conjugate. Clearly, this conjugate acts as an artificial fibrinogen, aggregating the platelets at a high efficiency rate. Curves b and c on FIG. 6 are controls illustrating the effectiveness of the conjugate as an artificial fibrinogen. In Curve b, the "model molecule" was first mixed with Fab fragments of rabbit antibody which had been made against the terminal portion of the gamma chain of human fibrinogen. These Fab fragments react with the peptide side chains on the conjugate, preventing them from interacting with the ADP-treated human platelets thereby inhibiting the aggregation reaction. This is evident from the almost flat response shown as Curve b on FIG. 6.

The alternate control, inhibiting the artificial fibrinogen reaction using the peptides themselves, is shown in Curve c. In this reaction, the platelets were mixed with unconjugated peptides and then the conjugate was used in attempt to aggregate the platelets. Again, the near zero slope of Curve c illustrates that the aggregation reaction by the artificial fibrinogen conjugate is inhibited by the peptides themselves.

EXAMPLE 6

Figure 7:
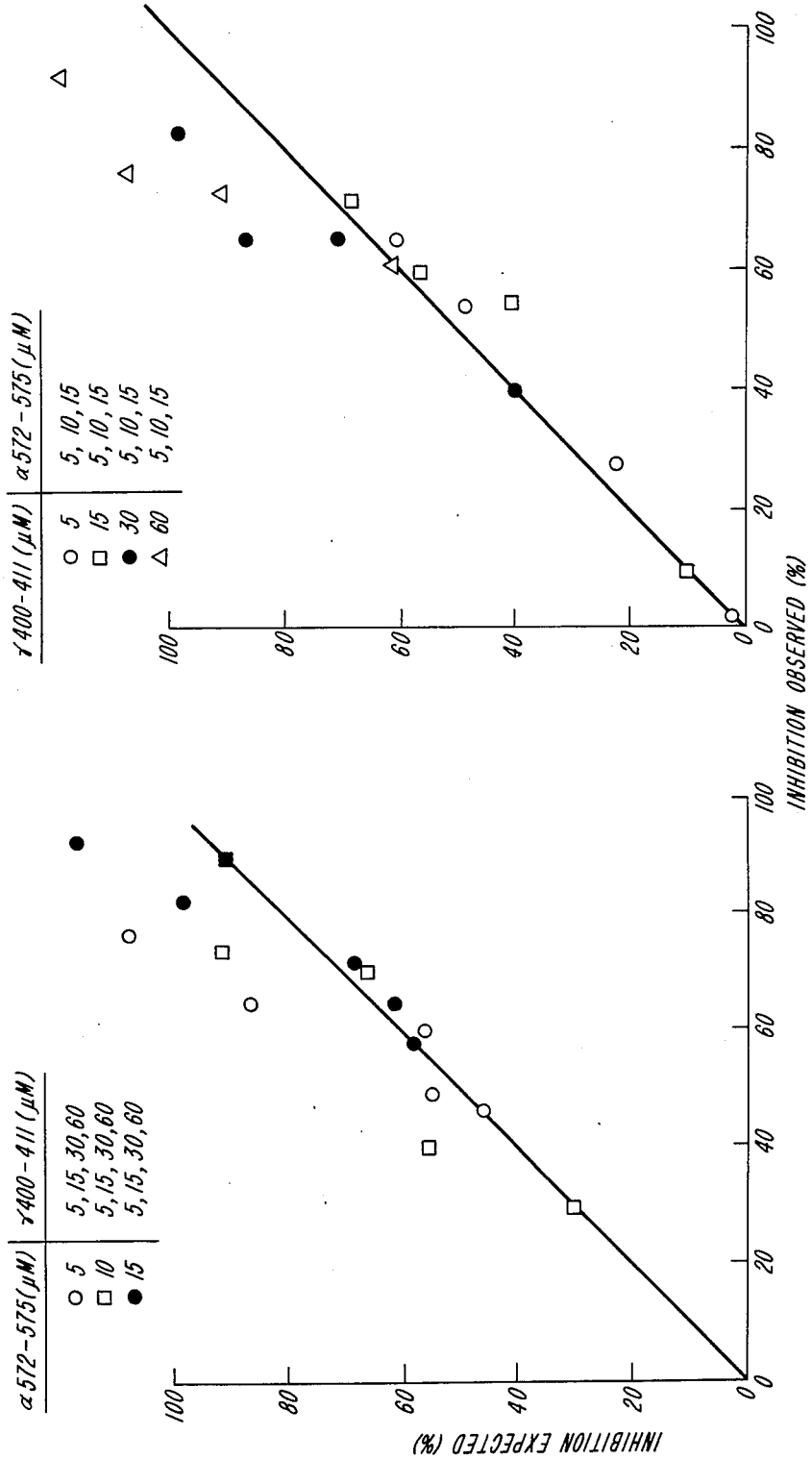
FIG. 7 shows two graphs which illustrate the inhibitory effect on fibrinogen binding by a mixture of two different peptides.

This Example illustrates that mixtures of peptides, such as can be maintained on a single conjugate backbone, can cause effects which are similar to the peptides individually. The two graphs in FIG. 7 illustrate mixtures of a peptide identical to the last 12 residues of the gamma chain of human fibrinogen and the known four residues of the alpha chain of human fibrinogen. These peptides are distinct in structure and will react with complementary receptor sites to block access of natural ligand, such as fibrinogen. The graphs are plots of expected percent inhibition on the vertical axis (the inhibition of the binding reaction which would be expected if there is no interaction between the two peptides) and the experimental observed percent inhibition on the horizontal axis. If there is no interactive effect between the two peptides, one would expect all the points to lie on the 45° line. As is evident from the graphs, the data appears to follow these 45° lines. This type of testing is useful as the step just prior to forming a mixed peptide conjugate.

EXAMPLE 7

Figure 8:
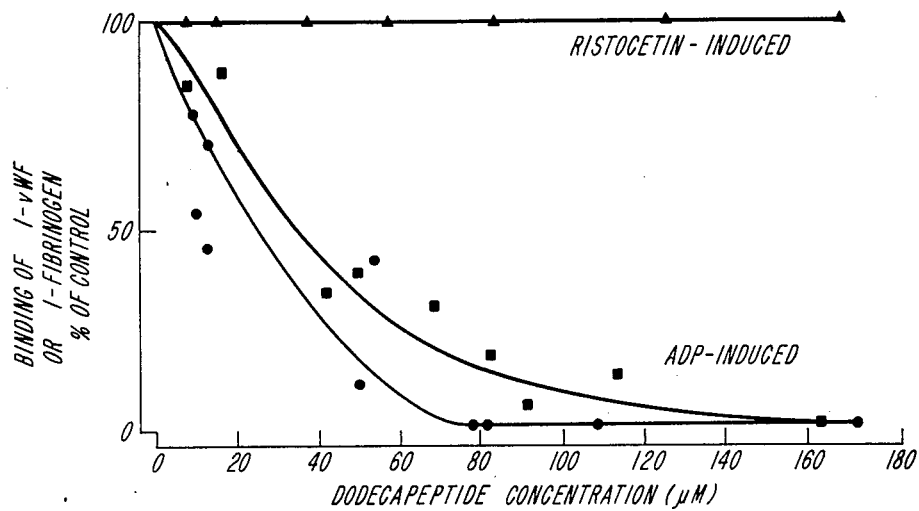
FIG. 8 illustrates that the same membrane may have different receptor sites if treated with different materials so that a peptide complementary to one site may not react with the other.

This Example illustrates that a peptide can be used to inhibit binding of von Willebrand factor to ADP-treated human platelets. FIG. 8 illustrates the level of inhibition of $^{125}$I-labelled von Willebrand factor or fibrinogen binding to ADP-modified human platelets by incubation with a synthetic dodecapeptide

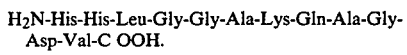

H$_2$N-His-His-Leu-Gly-Gly-Ala-Lys-Gln-Ala-Gly-Asp-Val-C OOH.

The FIGURE also illustrates that the same dodecapeptide does not inhibit the binding of $^{125}$I-labelled von Willebrand factor to ristocetin-modified human platelets.

Specifically, FIG. 8 shows that addition of various levels of the dodecapeptide to $10^8$ human platelets/0.55 ml treated with 5 mM of ADP five minutes prior to the addition of 14 μg of $^{125}$I-labelled von Willebrand factor ( — ) or μ33 g of $^{125}$I-labelled fibrinogen ( — ) will cause substantial binding inhibition. The FIGURE also shows that the dodecapeptide does not inhibit the binding of $^{125}$I-labelled von Willebrand factor to human platelets treated with 0.6 mg/ml ristocetin ( — ).

One explanation for these results is that the binding of the dodecapeptide to the ADP-modified human platelets prohibits binding of fibrinogen or von Willebrand factor by sterically blocking the protein binding site. However, the ristocetin-modified human platelets are not hindered in binding of von Willebrand factor. This experiment suggests ristocetin causes a different modification of the platelets than ADP or thrombin so that von Willebrand factor binds to ristocetin-modified platelets through a different binding site than it does to ADP or thrombin treated platelets. These experiments indicate that distinct binding domains on von Willebrand factor can participate in its binding to human platelets modified with thrombin, ADP, or ristocetin. Small peptides analogous to these domains can block one or two binding sites responsible for interaction of von Willebrand factor with platelets.

EXAMPLE 8

Figure 9:
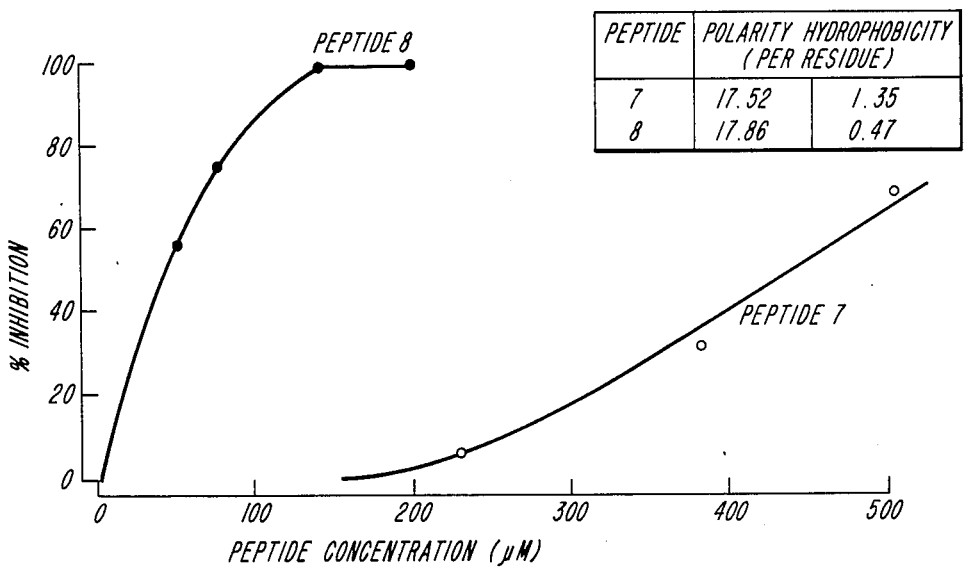
FIG. 9 illustrates that changing the hydrophobicity of a peptide may change its inhibitory characteristics.

This Example shows that changing the hydrophobicity of the peptide can change its effectiveness in inhibiting fibrinogen binding. Modification of the intermediate residues which are not involved in the actual reaction can, therefore, be modified to increase or decrease effectiveness of the conjugate. FIG. 9 illustrates the effect of the change of hydrophobicity. Both peptide 7 and peptide 8 are based on the peptide which is identical to residues 400–411 of the gamma chain of human fibrinogen. In peptide 7, residue 403 is changed from a glycine to a glutamine and residues 404, 405, 408 and 409 are changed from glycine or alanine to leucine. This causes the peptide to have more hydrphobocity. Peptide 8 also has residues 403–405 and 407 and 408 modified. In the case of peptide 8, all of these residues have been replaced by threonine. The threonine substitution keeps the polarity of the peptide substantially identical but yields a much lower hydrophobicity. As is evident from the FIGURE, the change in hydrophobicity has a marked effect on the inhibition effectiveness. The more hydrophilic (less hydrophobic) peptide, peptide 8, is much more effective in inhibition than peptide 7. This type of modification of the peptides can be useful to tailor the peptide side chains of the conjugate in order to form the most effective molecule for a particular purpose.

EXAMPLE 9

Figure 10:
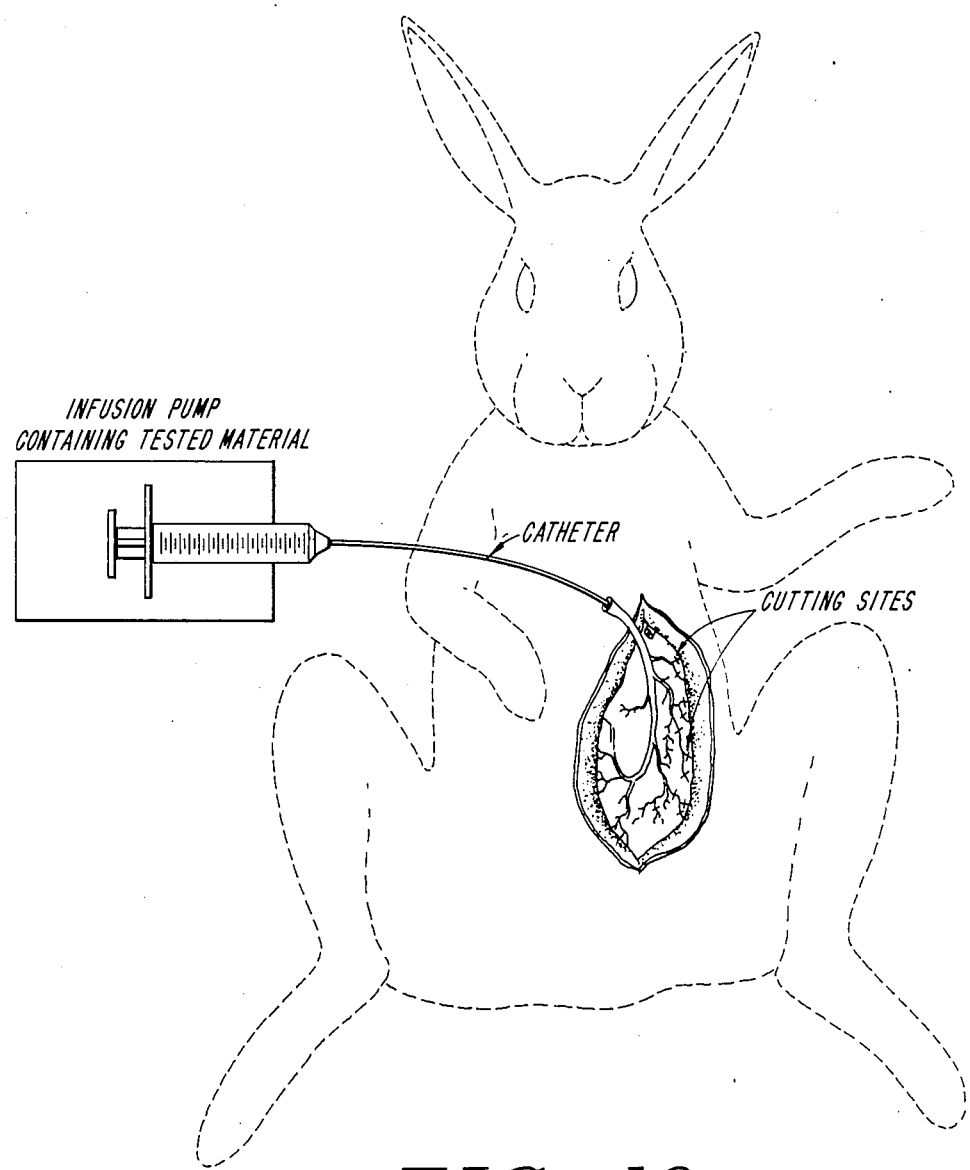
FIG. 10 is a schematic illustration of an in vivo experiment using a system for rabbits superior mesenteric artery perfusion.

This Example illustrates an in vivo model of mesentric artery perfusion in a rabbit. The experimental model employed involved anesthesized white New Zealand rabbits, weighing about 2.0 kg, and fed standard diet. The right femoral artery was canulated for blood pressure measurement and blood sampling. A midline abdominal incision was made to exteriorize the small intestine, the mesentery was draped over a microscope table, and superfused continuously with saline at 37° C. A polyethylene catheter (external diameter 1.09 mm, internal diameter 0.38 cm, Clay-Adams, Pezo, NJ) was inserted into the main branch of the superior mesenteric artery, permitting infusion into the territory supplied by the rest of the mesenteric artery (FIG. 10). The mesenteric vessels, demonstrated by infusing isotonic saline containing 1% (w/v) Evans blue in 3% (w/v) bovine plasma albumin, were observed through a microscope at a 65 x magnification. Small arteries of 100–200 μm external diameter were cut one third across with a surgical blade at the junction of the mesentery with the intestine. The time in seconds was determined from incision until the bleeding was arrested by a spontaneously formed hemostatic plug. Infusions of selected agents tested for their effects on platelet activation were through the mesenteric cannula with a constant volume Harvard pump at a flow rate of 0.11 ml/min. Three animals were used for each dose unless otherwise indicated. Blood pressure, hematocrit, and platelet count were measured prior to and after bleeding time determinations.

Figure 11:
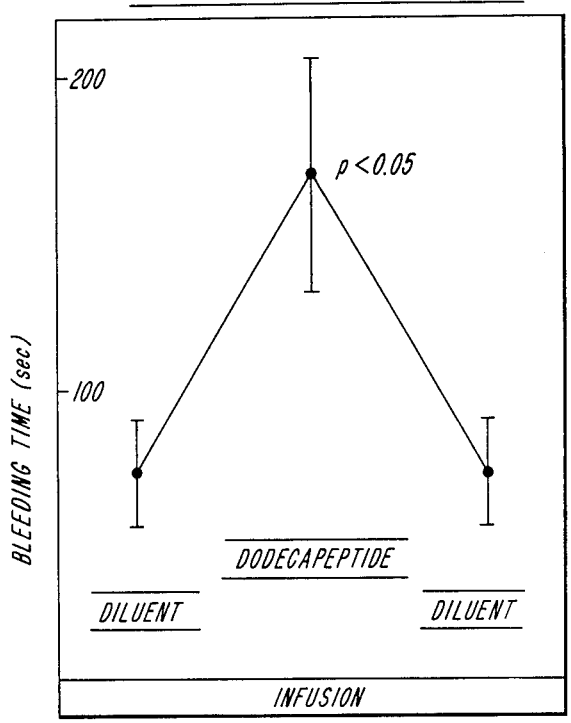
FIG. 11 is a graph that illustrates that perfusion with a peptide which inhibits hemostatic plug formation prolongs the bleeding time in the in vivo perfusion system illustrated in FIG. 10.

FIG. 11 shows the results of the in vivo rabbit mesenteric artery perfusion test. The bleeding time with infusion of pure diluent was less than a hundred seconds until a hemostatic plug formed, preventing bleeding. After infusion of the inhibitory peptide, the bleeding time rises to more than double its original time, showing inhibition of hemostatic plug formation. After the infusion of the peptide is replaced again by infusion of the diluent, the level of inhibition decreases dramatically, resuming its original level. The time to resume original bleeding time was approximately 20 minutes, showing clearance of the peptide in that time. This illustrates the need for a conjugate which has an extended lifetime and would therefore inhibit the hemostatic plug formation for a longer time period.

Figure 12:
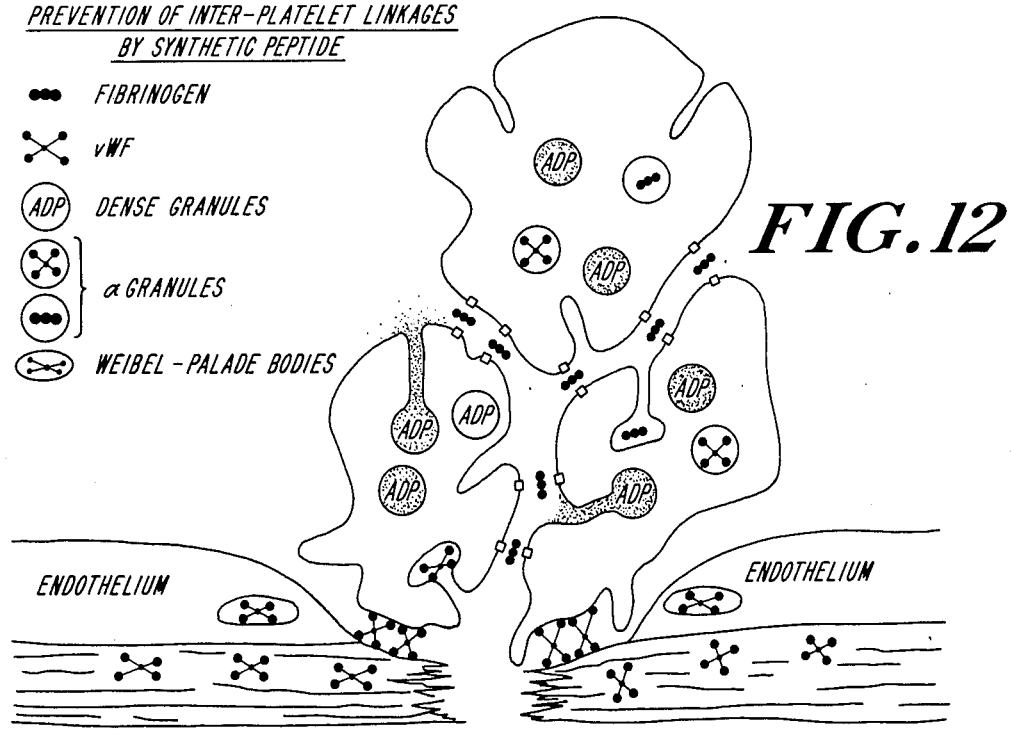
FIG. 12 is a schematic drawing which illustrates the sites of reaction and inhibition of hemostatic plug formation.

FIG. 12 is a schematic illustration of how the hemostatic plug is formed. The platelets, shown by the large irregular shaped objects, are activated from without and from within by ADP, which modifies their membrane sites. Normally fibrinogen, shown by the three filled dots, would react with receptor sites on the platelets, linking them to form a hemostatic plug which would seal off the cut in the endothelium layer. However, the small squares which represent the inhibitor peptides are at the receptor sites on the platelets and, therefore, block the aggregation reaction of the fibrinogen. In like manner, the inhibitors could react with receptor sites for the von Willebrand factor, preventing adhesion of the platelets to the blood vessel wall.

EXAMPLE 10

In order to determine biologic activity of preformed conjugates of synthetic peptides and macromolecular carriers, an ex vivo perfusion system patterned after Baumgartner (*Microvascular Res.*, 1973, 5:167) can be employed. This system consists of segments of blood vessels from which the endothelium (internal lining) is stripped off. Usually, excised rabbit aorta is used in this system, but segments of other blood vessels obtained during surgery can be employed.

These vessel segments are placed on the rod positioned within a small animal perfusion chamber which permits regulation of wall-shear rates. The blood drawn from the antecubital vein of a human volunteer (usually 30 ml volume) is pumped through the perfusion chamber by a peristaltic roller pump. To maintain the fluidity of blood, an appropriate anticoagulant (sodium citrate 0.11 M or hirudin 3 U/ml) is added. The temperature of the perfusion system is kept at 37° C. (body temperature). The tested material is added to the blood prior to its passage through the perfusion chamber. The influence of tested material on the interaction of blood cellular elements (platelets) or plasma proteins (e.g., von Willebrand factor, fibrinogen and other coagulation factors) with the vessel wall is assessed by morphometric evaluation in the case of platelets, as described by Baumgartner (see above); by the use of platelets radiolabeled with Indium prior to the perfusion run, as described by Sixma et al., (*Blood*, 1984, 63:128); and by the use of plasma proteins labeled with $^{125}$Iodine or $^{131}$Iodine and radioactivity measurement of the blood vessel wall segments directly or indirectly by autoradiography.

As the examples clearly indicate, the conjugates can be used both as inhibitory molecules and in place of naturally occurring molecules. This flexibility allows the tailoring of conjugates to specific uses and for a broad range of applications.

The examples set forth just some of the uses of this conjugate system and those skilled in the art may develop modifications or additions to the uses described herein. Such modifications or additions are within the scope of the following claims.

What is claimed is:

1. A method of inhibiting the in vivo reaction in a vertebrate between a naturally occurring protein and a protein or lipid receptor for said naturally occurring protein in said vertebrate comprising the steps of:
    administering a conjugate formed of
        one or more synthetic peptide analogs each of which is an analog of the interaction site on said naturally occurring protein for said receptor and is complementary to said receptor in said vertebrate, said synthetic peptide analog having a characteristic half-life in the circulatory system of said vertebrate; and
        a nonimmunogenic carrier molecule selected from a group consisting of proteins, polysaccharides, lipids, glycolipids, phospholipids, and neutral lipids;
    wherein said conjugate does not cause an immunological response in said vertebrate and is reactive with said receptor in said vertebrate through said synthetic peptide ananlog while being characterized by a half-life in the circulatory system of said vertebrate which is longer than the half-life of said synthetic peptide analog, and whereby said conjugate inhibits the reaction of said naturally occurring protein by competing with said naturally occurring protein for reaction with said receptor in said vertebrate.

2. The method of claim 1 wherein said peptides are conjugated to said carrier molecule by one or more sulfhydryl groups.

3. The method of claim 1 wherein said peptides are conjugated to said carrier molecule by one or more amino groups.

4. The method of claim 1 wherein said in said vertebrate are selected from a group consisting of sites of biological activity of binding proteins, inhibitory proteins, hormones, cofactors, and activators, and cellular receptors.

5. The method of claim 1 wherein said carrier molecule is selected from a group consisting of albumin, immunoglobin and other proteins.

6. A method of replacing a naturally occurring protein which is reactive in vivo with a receptor for said naturally occurring protein in a vertebrate with a synthetic conjugate, said method comprising the step of:
    administering said synthetic conjugate to said vertebrate, said conjugate being formed of
    one or more synthetic peptide analogs each of which is an analog of the interaction site on said naturally occurring protein for said receptor and is complementary to said receptor in said vertebrate, said synthetic peptide analog having a characteristic half-life in the circulatory system of said vertebrate; and
    a nonimmunological carrier molecule selected from a group consisting of proteins, polysacchrides, lipids, glycolipids, phospholipids, and neutral lipids;
    wherein said conjugate retains the reactivity of said synthetic peptide analog and does not cause immunological response in said vertebrate while being characterized by a half-life in the circulatory system of said vertebrate which is longer than the half-lives of said synthetic peptide analogs, and whereby said conjugate functionally replaces said naturally occurring protein in reactions with said receptor in said vertebrate.

7. The method of claim 6 wherein said peptides are conjugated to said carrier molecule by one or more sulfhydryl groups.

8. The method of claim 6 wherein said peptides are conjugated to said carrier molecule by one or more amino groups.

9. The method of claim 6 wherein said receptor in said vertebrate is selected from a group consisting of sites of biological activity of binding proteins, inhibitory proteins, hormones, cofactors, activators, and cellular receptors.

10. The method of claim 6 wherein said carrier molecule is selected from a group consisting of albumin, immunoglobin and other proteins.

11. The method of claim 6 wherein said carrier molecule has only one of said peptides conjugated thereto.

12. The method of claim 6 wherein said carrier molecule has at least two of said peptides conjugated thereto, and said peptides are complementary to at least two distinct receptors.

13. A method of constructing a conjugate which is nonimmunogenic and reactive with a receptor in a vertebrate and is characterized by an extended life-time in the circulatory system of said vertebrate, said method comprising the steps of:

A. indentifying a receptor on a protein or lipid in a vertebrate, said receptor being an interaction site on said protein or lipid for the interaction between a peptide or peptide unit and said protein or lipid;
B. forming a synthetic peptide analog of said peptide or peptide unit which interacts with and is complementary to said receptor, said synthetic peptide having a characteristic half-life in the circulatory system of said vertebrate; and
C. forming a conjugate of said synthetic peptide analog and a nonimmunogenic carrier molecule selected from a group consisting of proteins, polysaccharides, lipids, glycolipids, phospholipids, and neutral lipids, whereby said conjugate has a half-life in the circulatory system of said vertebrate which is greater than the characteristic half-life of said synthetic peptide analog and said conjugate does not cause an immunological response in said vertebrate.

14. The method of claim 13 wherein said conjugating step comprises conjugating said peptides to said carrier molecule by one or more sulfhydryl groups.

15. The method of claim 13 wherein said conjugating step comprises conjugating said peptides to said carrier molecule by one or more amino groups.

16. The method of claim 13 wherein said carrier molecule is selected from a group consisting of albumin, immunoglobulin and other proteins.

17. The method of claim 13 wherein said receptor in said vertebrate is selected from a group consisting of sites of biological activity of binding proteins, inhibitory proteins, hormones, cofactors, activators, and cellular receptors.

18. The method of claim 13 wherein said carrier molecule has only one of said peptides conjugated thereto.

19. The method of claim 13 wherein said carrier molecule has at least two peptides conjugated thereto, and said peptides are complementary to at least two, distinct receptors in said vertebrate.

* * * * *